United States Patent [19]

Pfeiffer

[11] 4,221,740
[45] Sep. 9, 1980

[54] PROCESS FOR THE PREPARATION OF SERINOL (1,3-DIHYDROXY-2-AMINOPROPANE)

[75] Inventor: Heinrich Pfeiffer, Berlin, Fed. Rep. of Germany

[73] Assignee: Schering Aktiengesellschaft, Berlin and Bergkamen, Fed. Rep. of Germany

[21] Appl. No.: 943,094

[22] Filed: Sep. 18, 1978

[30] Foreign Application Priority Data

Sep. 21, 1977 [DE] Fed. Rep. of Germany ....... 2742981

[51] Int. Cl.² .............................................. C07C 85/11
[52] U.S. Cl. ........................... 260/584 R; 260/583 M; 260/583 N
[58] Field of Search ........... 260/584 R, 583 M, 583 N

[56] References Cited

U.S. PATENT DOCUMENTS

| 2,587,572 | 2/1952 | Tryon | 260/583 M X |
| 3,564,062 | 2/1971 | Tindall | 260/584 R X |

OTHER PUBLICATIONS

Handbook of Chemistry and Physics, 52nd Edition, p. C-444, (1971-1972).
Smith, "The Chem. of Open-Chain Org. Nitrogen Cmpds.", vol. II, p. 65, (1966).
Astle, "Ind. Org. Nitrogen Cmpds.", pp. 19-20, (1961).
Ginsburg, "Concerning Amines", pp. 42-43, (1967).
Schmidt et al., "Berichte", vol. 52, pp. 389-399, (1919).

*Primary Examiner*—John Doll
*Attorney, Agent, or Firm*—Millen & White

[57] ABSTRACT

The sodium salt of 1,3-dihydroxy-2-nitropropane is catalytically hydrogenated in an inert solvent to produce 1,3-dihydroxy-2-aminopropane, which can be isolated in crystalline form.

10 Claims, No Drawings

PROCESS FOR THE PREPARATION OF SERINOL (1,3-DIHYDROXY-2-AMINOPROPANE)

BACKGROUND OF THE INVENTION

The present invention relates to a process for the preparation of 1,3-dihydroxy-2-nitropropane.

1,3-Dihydroxy-2-aminopropane, also called serinal in the literature, is a small, physiologically well compatible base which has gained increasing significance as an intermediate for the production of physiologically very highly compatible X-ray contrast media. In this regard, see German Pat. No. 2,547,789 and German Patent Application No. P 26 28 517.6, corresponding to U.S. Application Ser. No. 806,384, filed on June 14, 1977, which disclose the advantageous properties of serionl-containing X-ray contrast media and processes for the preparation thereof. The disclosures of these documents are incorporated by reference herein with respect to their discussion of this use of serinol.

Herefore, the literature has described only extremely expensive multistage syntheses for the preparation of serinol. Consequently, these are technically and industrially useless. Moreover, they yield only low quantities of product.

In one process, serionl oxalate or hydrochloride was isolated in a 15% yield by Piloty el al ("Ber. dtsch. Chem. Ges." [Reports of the German Chemical Society] 30: 2061 [1897]). They started with dihydroxyacetone, prepared the dihydroxyacetone oxime and subsequently reduced this with sodium amalgam.

A different synthesis is described by Schmidt et al ("Ber. dtsch. Chem. Ges." 52: 389 [1919]). In this process, paraformaldehyde and nitromethane are condensed in the presence of aqueous potassium hydroxide solution, and the reaction product is converted without isolation of the intermediates into the sodium salt of 1,3-dihydroxy-2-nitropropane. The sodium salt, serving as the starting compound for the subsequent reaction steps, is obtained in a 91% yield with 2 moles of methanol. To convert the nitro group into the amino group, it is necessary in accordance with this reference to produce the free nitro compound prior to hydrogenation.

The conversion of the sodium salt of a nitro compound into the free nitro compound, however, is quite generally accompanied by secondary reactions, which can be so predominant as to even become the primary reaction. According to Houben-Weyl, vol. X/1: 456 (1969), the free nitropropanediol cannot be produced with mineral acids; or, if it is so produced, the reaction yields only very low quantities of desired product. Schmidt el al react the Na salt with salicylic acid in ether, thus isolating the not-yet-completely pure 1,3-dihydroxy-2-nitropropane in a 59% yield. The subsequent catalytic hydrogenation is best accomplished, in accordance with the Schmidt et al reference, with a pelladium/barium sulfate catalyst, in an oxalic acid solution. In a neutral solution, the hydrogenation takes place very reluctantly, and in an alkaline or mineral acid solution, the hydrogenation fails altogether.

From the oxalic acid solution, the neutral oxalate of 1,3-dihydroxy-2-aminopropane is isolated in a 93% yield. Finally, the serinol is liberated therefrom as a viscous liquid by the precipitation of barium oxalate by addition of barium hydroxide solution. No data regarding the yield from this completeprocess are set forth.

SUMMARY OF THE INVENTION

Accordingly, it is an object of this invention to provide an improved, economically exploitable process (i.e., having high yields; ease of operation; etc.) for the preparation of serinol.

Upon further study of the specification and appended claims, further objects and advantages of this invention will become apparent to those skilled in the art.

These objects have been attained by providing in a process for the preparation of 1,3-dihydroxy-2-aminopropane which comprises catalytically hydrogenating a corresponding 2-nitropropane compound, an improvement comprising catalytically hydrogenating the sodium salt of 1,3-dihydroxy-2-nitropropane.

DETAILED DISCUSSION

It has been found, surprisingly, that it is possible to utilize under suitable conditions, in place of the conventional free 2-nitropropane-1,3-diol which is accessible only with difficulties, the technically and industrially readily obtainable, pure sodium salt for hydrogenation to produce serinol. The improvement provided by this invention resides, on the one hand, in the technically simple manufacture of serionol in a single-stage process and, on the other hand, in that, by the suppression of secondary reactions, a product of a very high degree of purity is obtained in yields of up to 82%. Moreover, for the very first time, the product is present in crystalline form.

The process of this invention, in contrast to the above-described three-stage procedure, is a single-stage process wherein the sodium salt of 1,3-dihydroxy-2-nitropropane, which can contain 2 moles of water or 2 moles of methanol, is hydrogenated to serinol under conventional conditions for reducing a nitro group to an amino group by catalytic hydrogenation. See, for example, H. Wilnes Houben-Weyl XI/1, 384 (1957), whose disclosure is incorporated by reference herein for all details of the conventional reduction unless otherwise noted herein.

To neutralize the sodium hydroxide solution produced during the hydrogenation, a stoichiometric amount of a buffered acid such as ammonium chloride, ammonium sulfate, ammonium phosphate, inter alia, can be added to the reaction mixture. The sodium salts of these acids, e.g., NaCl, $Na_2SO_4$, etc., should be readily separable during the working up of the hydrogenation batches. However, the hydrogenation can be conducted in a similarly satisfactory manner without the addition of a compound which neutralizes the sodium hydroxide solution, or with the addition of a less than stoichiometric amount of such a compound. In any event, however, the residual sodium hydroxide solution is neutralized prior to distillation of the reaction mixture.

The hydrogenation is conducted using conventional, metal-containing hydrogenation catalysts. Suitable hydrogenation catalysts include, for example: nickel-, palladium-, platinum-, or rhodium-containing catalysts, e.g. Pd-barium sulfate, Pt(IV) oxide, Rh-charcoal, and preferably Raney nickel or mixed nickel catalysts.

Suitable as the reaction medium are all inert solvents conventionally employed in hydrogenation reactions, as long as they are capable of dissolving serinol, e.g., lower alcohols, such as methanol, ethanol, isopropanol; water; and mixtures thereof. Since highly concentrated solutions are disadvantageous in hydrogenation reactions, 5-25 wt. % Na salt solutions based on the total weight of salt and solvent are expediently employed.

The hydrogenation can be conducted at room temperature, as well as at lower or higher temperatures. Preferably, a temperature of 0°-80° C. is used to carry out the reaction which takes place exothermically. The hydrogenation can be conducted under normal as well as elevated pressure. Typically, a hydrogen pressure of 1-100 atmospheres is considered advantageous. Generally suitable reactions times are 1-5 hours, and reaction yields are 60-85% based on starting nitro compound.

After the hydrogenation, the reaction mixture is worked up as usual, optionally with the addition of a neutralizing agent. For example, the solvent can be distilled off, and the thus-formed inorganic salt can be precipitated and separated. The crude serinol can optionally be purified by distillation.

The product wihich has been separated from the hydrogenation medium can be obtained in a crystalline form by allowing the same to stand for a longer period of time. Alternatively, the crystalline form can also be obtained, for example, by inoculation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Preparation of the Starting Compound

A solution of 48.8 g (0.8 mol) of nitromethane in 750 cc of methanol is combined with 83 g of paraformaldehyde (2.76 mol). After adding 15 drops of 33% aqueous KOH, the reaction mixture is heated to boiling under agitation. With ice cooling and stirring, a solution of 54 g of sodium methylate (1.0 mol) in 350 cc of methanol is added dropwise to the clear solution. The sodium nitropropanediol crystallizes with 2 moles of methanol.

Yield: 151 g=91% theory.

200 g of the crude compound is dissolved in 1 liter of water. The dark-brown solution is concentrated to a slurry-like consistency. The thus-crystallized precipitate is vaccum-filtered and washed with a very small amount of water. After drying at 30° C. (under vacuum), the yield is 138.7 g (76.7%) of the sodium salt of 1,3-dihydroxy-2-nitropropane as the dihydrate. Melting point: 110°-112° C. (under decomposition).

EXAMPLE 1

Preparation of 1,3-Dihydroxy-2-Aminopropane=Serinol 71.6 g (400 mol) of Na nitropropanediol dihydrate is suspended in 900 ml of methanol. After introduction into a pressure autoclave, the charge is combined with 17.1 g (320 mmol) of ammonium chloride, as well as 8 g of Raney nickel. The hydrogenation is initiated at a hydrogen pressure of 70 atmospheres and at room temperature. The hydrogen absorption is terminated within a few hours. Subsequently, the catalyst is separated, and the solution is combined with 4.3 g (80 mmol) of ammonium chloride. The methanol is distilled off under vacuum, and the oily residue is flushed with 80 ml of isopropanol on a porous glass plate. The sodium chloride is vacuum-filtered and discarded. Under vacuum, isopropanol is distilled off from the filtrate. The serinol is distilled under vacuum at b.p.$_7$ at 136°-138° C. Yield: 27.5 g=75.5%. The product purity, as determined by gas chromatography was 99.6%. After allowing the serinol to stand for a longer period of time, or upon inoculation, it crystallizes; melting point: about 50° C.

EXAMPLES 2-8

Analogously to Example 1, a series of similar experiments were conducted to prove the wide range of variations to which the process can be subjected.

The following table lists the details and results of all Examples.

TABLE

Hydrogenation Experiments Used in each case: 0.4 mole Na Salt × 2 H$_2$O (I) $\triangleq$ 71.6 g.
or 0.4 mole Na Salt × 2 MeOH (II) $\triangleq$ 82.8 g.

| Example No. | Na Salt | Solvent Type | Solvent Amount ml. | Neutralizing Agent Type | Neutralizing Agent % a | Initial H$_2$ Pressure atm. | Max. Temp. °C. | Yield After Dist. % | Purity Acc. to Gas Chrom. |
|---|---|---|---|---|---|---|---|---|---|
| 1 | I | MeOH | 900 | NH$_4$Cl | 80 | 70 | 27 | 75.5 | 99.6 |
| 2 | I | i-PrOH | 900 | NH$_4$Cl | 95 | 70 | 27 | 64.8 | 99.9 |
| 3 | I | H$_2$O | 900 | (NH$_4$)$_2$SO$_4$ | 95 | 70 | 27 | 63.7 | 99.6 |
| 4 | I | EtOH | 900 | NH$_4$Cl | 80 | 70 | 27 | 70.2 | 98.0 |
| 5 | I | MeOH | 900 | NH$_4$Cl | 0 | 70 | 27 | 71.9 | 99.9 |
| 6 | I | MeOH | 900 | NH$_4$Cl | 100 | 25 | 10 | 82.0 | 99.9 |
| 7 | II | MeOH | 900 | NH$_4$Cl | 80 | 70 | 27 | 73.0 | 98.7 |
| 8 | I | MeOH | 450 | NH$_4$Cl | 80 | 7 | 44 | 77.7 | 99.4 | a = % of the neutralizing agent added prior to hydrogenation.

EXAMPLE 9

In a 1-liter autoclave having a magnetic agitator unit, a suspension of 41.4 g=0.2 mol of sodium nitropropanediol-1,3 having about 2 moles of crystalline methanol, is hydrogenated, in 450 ml of methanol, with 8.6 g-0.16 mol of ammonium chloride and 4 g of a 10% palladium charcoal catalyst, under an initial hydrogen pressure of 70 atmospheres and at room temperature. After a few hours, the hydrogen absorption is arrested at 32 atmospheres. The product is worked up in accordance with Example 1 with the addition of 2.15 g of ammonium chloride and yields, after distillation, 13.1 g=71.5% of theory of serinol; b.p.$_6$ 134°-137° C.; purity according to gas chromatography: 98.5%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing 1,3-dihydroxy-2-aminopropane consisting essentially of catalytically hydrogenating the sodium salt of 1,3-dihydroxy-2-nitropropane.

2. The process of claim 1, wherein the hydrogenation is carried out in an inert solvent.

3. The process of claim 1 wherein a buffered acid is present during the hydrogenation in an amount sufficient to at least partially neutralize the NaOH which is formed.

4. The process of claim 2 wherein the concentration of the sodium salt in the solvent is 5–25 wt. %.

5. The process of claim 1, wherein the reaction temperature is 0°–80° C. and the hydrogen pressure is 1–100 atmospheres.

6. The process of claim 2, wherein the solvent is a lower alcohol, water or a mixture thereof.

7. The process of claim 3, wherein the buffered acid is an ammonium salt of an anion whose sodium salt is readily separated from the reaction medium after the completion of the hydrogenation reaction.

8. The process of claim 1 which further comprises separating the 1,3-dihydroxy-2-aminopropane from the reaction medium after the completion of the hydrogenation reaction.

9. The process of claim 8 which further comprises allowing the separated aminopropane product to stand for a period of time sufficient to produce a crystalline form of the aminopropane.

10. The process of claim 1 which comprises conducting the hydrogenation as a 5–25 wt.% solution of the sodium salt of 1,3-dihydroxy-2-nitropropane in methanol with a Raney nickel catalyst, under pressure at a maximum temperature of up to 80° C., in the presence of an amount of ammonium chloride, sufficient to neutralize 80–100 molar percent of the NaOH produced, and isolating the thus-produced 1,3-dihydroxy-2-aminopropane from the neutralized reaction mixture by distillation.

* * * * *